(12) United States Patent
Rowe et al.

(10) Patent No.: US 6,200,603 B1
(45) Date of Patent: Mar. 13, 2001

(54) COMESTIBLE CAPSULES HAVING FLAVORED COATINGS

(75) Inventors: Dennis Rowe; Kelvin Royce Garnett; Kate Hale, all of Swindon (GB)

(73) Assignee: R. P. Scherer Corporation, Basking Ridge, NJ (US)

( * ) Notice: Subject to any disclaimer, the term of this patent is extended or adjusted under 35 U.S.C. 154(b) by 0 days.

(21) Appl. No.: 09/404,426

(22) Filed: Sep. 23, 1999

Related U.S. Application Data

(63) Continuation of application No. PCT/GB98/00916, filed on Mar. 25, 1998.

(30) Foreign Application Priority Data

Mar. 25, 1997 (GB) .................................................. 9706149

(51) Int. Cl.[7] .............................. A61K 9/48; A61K 9/30; A61K 9/42; A61K 9/40; A61K 9/36
(52) U.S. Cl. .......................... 424/463; 424/475; 424/476; 424/478; 424/479
(58) Field of Search .................................... 424/439, 440, 424/463

(56) References Cited

U.S. PATENT DOCUMENTS

| 4,816,259 | * | 3/1989 | Matthews et al. | 424/463 |
| 5,827,852 | * | 10/1998 | Russell et al. | 514/255 |
| 5,900,251 | * | 5/1999 | Raissen | 424/456 |

FOREIGN PATENT DOCUMENTS

| 0 317 510 A2 | | 5/1989 | (EP) . |
| 0374359 | * | 6/1990 | (EP) . |
| 0 374 359 A2 | | 6/1990 | (EP) . |
| 2155286 | | 5/1973 | (FR) . |
| 2 535 608 | | 5/1984 | (FR) . |
| 2283899 | * | 5/1995 | (GB) . |
| 84/03417 | | 9/1984 | (WO) . |
| 95/00123 | | 1/1995 | (WO) . |
| 95/12380 | | 5/1995 | (WO) . |

* cited by examiner

*Primary Examiner*—Thurman K. Page
*Assistant Examiner*—S. Tran
(74) *Attorney, Agent, or Firm*—Donald O. Nickey; Daniel N. Christus

(57) ABSTRACT

A coated capsule is disclosed comprising a gelatin shell with a flavored coating. A sugar or sugar substitute is included in the material of the shell and that of the coating to stabilize both compositions and the junction therebetween.

13 Claims, No Drawings

COMESTIBLE CAPSULES HAVING FLAVORED COATINGS

RELATED APPLICATIONS

This Application is a Continuation of International Application No. PCT/GB98/00916, filed Mar. 25, 1998 (claiming priority from British Application No. 9706149.3, filed Mar. 25, 1997), now pending, which are hereby incorporated by reference.

FIELD OF THE INVENTION

This invention relates to comestible capsules for oral administration, and particularly such capsules having flavored or sweetened coatings. The invention is also concerned with such capsules which are intended for swallowing substantially intact, for release of the contents only when the capsule has reached the stomach.

BACKGROUND OF THE INVENTION

Many medicines are relatively unpleasant to taste, and in either tablet or encapsulated form, are masked by flavored coatings to make them more palatable. The present invention is concerned with the provision of a flavored coating around a gelatin capsule containing a fill composition which is typically liquid, but may be paste like or even solid in some circumstances. Gelatin shells provide a useful means for encapsulating such compositions, but there are problems in applying flavored coatings thereover. Particularly, typical coatings can provoke changes in the gelatin shell structure which can adversely affect the integrity of the capsule, and in some cases also the coating.

Typical gelatin shells used to encapsulate products comprise gelatin in combination with a plasticiser such as glycerine which, together with water preserve a degree of softness and flexibility in the shell material. Such shells are relatively easy to handle, but have disadvantages in terms of taste. This is particularly relevant to breath fresheners and, according to one aspect of the invention, a breath freshener is provided in the form of a filled gelatin capsule to which is applied a flavored coating. Such a coated capsule is especially suitable for swallowing prior to rupture of the capsule, whereby the capsule fill is not released until the capsule shell is broken down in the stomach.

SUMMARY OF THE INVENTION

For the above and other embodiments according to the present invention, the capsule shell formulation may be adapted, and a flavored coating applied to the capsule such that at least at the boundary between them, a stable bond is formed. This enables a substantially dry coating to be created which does not draw the water or plasticiser from the gelatin shell, with the resultant adverse consequences on the shell structure. This can be achieved by including in the capsule shell formulation a sugar or sugar substitute such as sorbitol, and matching it with an equivalent substance in the coating. The effect of this match is to effectively stabilize both the coating and shell formulations and in the gelatin, to prevent the migration of water and glycerine to the coating. In this way, the humectents are retained in the gelatin which can thus preserve its flexibility and palatability if retained in the mouth.

DETAILED DESCRIPTION OF THE INVENTION

As a general guide, we have established the following ranges of gelatin, glycerine, sugar or sugar substitute and water, as percentages by weight in the shell formulation, to provide a satisfactory base for a coating of for example sorbitol in solution:

| | |
|---|---|
| Gelatin | 33.00–58.00 |
| Glycerine | 16.00–31.00 |
| Sugar or sugar substitute eg Sorbitol | 15.00–30.00 |
| Water | up to 15.00 |

Preferably, the ratio of plasticiser (Glycerine+sugar or substitute) to Gelatin is in the range 0.7 to 1.2, preferably 0.8 to 1.0, with the ratio of sugar or substitute to Glycerine in the range 0.8 to 1.2.

We have found that in order to stabilize a soft gelatin shell to which a flavored coating is to be applied, a relatively high glycerine content must be established with a consequent reduction in the water content. Using sorbitol as the additional component in the shell, and as the basic component for the coating, we have established the following typical minimum levels of glycerine and sorbitol as percentages by weight in the dried shell formulation. The figures for gelatin and water in the formulation are also given.

| | |
|---|---|
| Glycerine | 17.7 |
| Sorbitol | 16.7 |
| Gelatin | 56.7 |
| Water | 8.9 |
| Total plasticiser: | 34.4%; |
| Plasticiser to Gel ratio: | 0.61 |

The glycerine and sorbitol levels can be further increased with consequential further reduction in the proportions of gelatin, and a typical shell formulation which is able to sustain its softness under an applied flavored coating of sorbitol is as follows.

| | |
|---|---|
| Glycerine | 21.0 |
| Sorbitol | 20.0 |
| Gelatin | 50.4 |
| Water | 8.6 |
| Total plasticiser: | 41.0%; |
| Plasticiser to Gel ratio: | 0.81 |

Experimentation has indicated that the glycerine and sorbitol levels can be increased beyond those quoted above, but we regard the following formulation as demonstrating typical maximum amounts of these components that can be retained in a viable shell structure embodying the invention.

| | |
|---|---|
| Glycerine | 29.3 |
| Sorbitol | 38.6 |
| Gelatin | 34.5 |
| Water | 7.6 |
| Total plasticiser: | 57.9%; |
| Plasticiser to Gel ratio: | 1.8 |

The use of increased glycerine content in gelatin shells to provide improved and stable softness is disclosed in our International Patent Publication No. WO95/00123, incorporated herein by reference. Formulations of the kind disclosed in that publication can be used in the exploitation of the present invention, having regard to the above guidance in respect of the additional stabilising component.

While in the above discussion the specified sugar or sugar substitute has been sorbitol, a variety of sugar alcohols or non-reducing saccharides or polyols may be used. For example:

sorbitol; polyglycerol; mannitol; xylitol; maltitol; isomalt; corn syrup, and Andrisorb™ (a proprietary mix of sorbitol, sorbitan and mannitol available from Roquette Freres).

As noted above, the flavored coating for products according to the invention is normally based on a sugar or a sugar substitute, and is typically applied to capsules as an aqueous solution in for example, a panning process. Pan coated gelatin capsules are disclosed in British published specification no. 2283899, incorporated herein by reference, and products may be coated according to the present invention using the techniques and parameters described therein. The eventual coating will typically be in crystalline form, and as such will tend to draw moisture from the capsule shell. By including water and a sugar or sugar substitute in both the coating material and the shell formulation, when the coating is applied a dynamic balance can be achieved. The coating will normally be applied wet, as in a pan coating process, and this itself assists in stabilising the interface between the coating and shell.

It is of course desirable to minimise the quantity of shell material in the coated product, and in this respect it is recognised that with a sufficiently stable interface and bond between the coating and shell, the coating will serve to reinforce the shell, and the shell to effectively seal the coating. Thus, if the shell thickness can be reduced such that its entire thickness is effectively bonded to the coating, then the resultant product will include a bare minimum of shell material.

Fill compositions for use in products according to the invention may take many forms, and in this respect reference is directed once again to published British specification no. 2283899. Additionally though, the present invention is suitable for compositions which are not intended to be released in the mouth, but for retention in the capsule until it reaches the stomach. This applies particularly to some breath freshening compositions such as parsley seed oil which can provide a very unpleasant flavour in the mouth despite being effective as a breath freshener from the stomach. The nature of the fill composition can of course have a direct effect on the integrity of the shell material, and oil based compositions such as parsley seed oil can have an additional softening effect on the shell. The presence of a sugar or a sugar substitute such as sorbitol in the shell can also serve to minimise the effect of both oil based and water based fill compositions on the shell.

EXAMPLE

A breath freshener in the form of a filled capsule embodying the present invention has the following formulations for the fill, shell and coating respectively:

|  | Quantity | %age |
| --- | --- | --- |
| Fill: |  |  |
| Aspartame | 0.825 mg | 0.516 |
| fractionated Coconut oil | 66.280 mg | 41.425 |
| Kaorich Beads | 10.888 mg | 6.8 |
| Levomethol BP/EP | 4.800 mg | 3.0 |
| Parsley Seed Oil | 0.250 mg | 0.156 |
| Pepperment flavour | 6.400 mg | 4.0 |
| Loders 7 (Hard Vegetable Fat) | 23.830 mg | 14.894 |
| Ascorbic Acid | 1.500 mg | 0.938 |
| Calcium Phosphate Dibasic | 41.750 mg | 26.094 |
| Lecithin thin (light) | 3.478 mg | 2.174 |
|  | 160.000 mg |  |
| Shell: |  |  |
| Glycerine | 19.98 mg | 19.98 |
| Sorbitol Syrup 70% | 27.19 mg | 27.19 |
| Gelatin | 52.83 mg | 52.83 |
|  | 100.00 mg |  |
| Coat: |  |  |
| Isomalt | 184.667 mg | 66.7 |
| Sorbitol | 92.33 mg | 33.3 |
|  | 277.000 mg |  |

The fill compositions in products according to the invention can of course themselves also include flavouring elements to make them more palatable if intended or required to be released in the mouth and additional elements could also be included in the shell composition with the same purpose. However, for products to be swallowed before the fill composition is released, it is of course the flavour of the coating that is of critical importance.

The complete disclosures of all patents, patent applications and publications are incorporated herein by reference as if each were individually incorporated by reference. The invention has been described with reference to various specific and preferred embodiments and techniques. However, it should be understood that many variations and modifications can be made without departing from either the spirit or scope of the invention.

What is claimed is:

1. A coated capsule containing a fill composition, the coated capsule comprising a gelatin shell having water and a plasticizer, wherein the ratio of plasticizer to gelatin in the shell composition ranges from 0.7 to 1.2, and a flavored coating thereon, wherein each of said flavored coating and shell material comprises a sugar or sugar substitute adapted to form a stable bond between the shell and the coating and to prevent the coating from drawing water or plasticizer from the gelatin shell.

2. A coated capsule according to claim 1 wherein the same sugar or sugar substitute is present in both the coating and the shell.

3. A coated capsule according to claim 1 or claim 2 wherein the composition of the shell material comprises:
   gelatin in an amount from 33 to 58% by weight;
   glycerine in an amount from 16 to 31% by weight;
   sugar or sugar substitute in an amount from 15 to 30% by weight; and
   water in an amount up to 15% by weight.

4. A coated capsule according to claim 3 wherein the quantity of water in the shell composition is up to 10% by weight.

5. A coated capsule according to claim 2 or claim 4 wherein the ratio of plasticizer to gelatin in the shell composition ranges from 0.8 to 1.0, wherein said plasticizer comprises both glycerine and the sugar or sugar substitute.

6. A coated capsule according to claim 3 wherein the ratio of sugar or sugar substitute to Glycerine ranges from 0.8 to 1.2.

7. A coated capsule according to claim 1 wherein the sugar or sugar substitute is selected from the group consisting of sorbitol, polyglycerol, mannitol, xylitol, maltitol, isomalt, and corn syrup and mixtures thereof.

8. A coated capsule according to claim 1 wherein the flavored coating comprises an aqueous solution of the sugar or sugar substitute.

9. A coated capsule according to claim 1 wherein the fill composition is a breath freshener.

10. A coated capsule according to claim 9 wherein the fill composition comprises parsley seed oil.

11. A coated capsule according to claim 4, wherein the ratio of sugar or sugar substitute to glycerine is in the range 0.8 to 1.2.

12. A coated capsule according to claim 5, wherein the ratio of sugar or sugar substitute to glycerine is in the range 0.8 to 1.2.

13. A coated capsule according to claim 1, wherein the fill composition comprises parsley seed oil.

* * * * *